(12) United States Patent
Brezinski et al.

(10) Patent No.: US 11,020,610 B2
(45) Date of Patent: Jun. 1, 2021

(54) POSITIONING DEVICE FOR USE IN THERAPEUTIC TREATMENT

(71) Applicant: Little Sparrows Technologies LLC, Winchester, MA (US)

(72) Inventors: Donna Brezinski, Winchester, MA (US); Gary Gilbert, Winchester, MA (US)

(73) Assignee: LITTLE SPARROWS TECHNOLOGIES INC., Winchester, MA (US)

( * ) Notice: Subject to any disclaimer, the term of this patent is extended or adjusted under 35 U.S.C. 154(b) by 578 days.

(21) Appl. No.: 15/739,319

(22) PCT Filed: Jun. 29, 2016

(86) PCT No.: PCT/US2016/040187
§ 371 (c)(1),
(2) Date: Dec. 22, 2017

(87) PCT Pub. No.: WO2017/004257
PCT Pub. Date: Jan. 5, 2017

(65) Prior Publication Data
US 2020/0038679 A1 Feb. 6, 2020

Related U.S. Application Data

(60) Provisional application No. 62/185,955, filed on Jun. 29, 2015.

(51) Int. Cl.
*A61N 5/06* (2006.01)
*A61F 7/08* (2006.01)

(52) U.S. Cl.
CPC .............. *A61N 5/0621* (2013.01); *A61F 7/08* (2013.01); *A61N 2005/0638* (2013.01);
(Continued)

(58) Field of Classification Search
CPC .......... A61N 5/0621; A61N 2005/0638; A61N 2005/0663; A61N 2005/0666;
(Continued)

(56) References Cited

U.S. PATENT DOCUMENTS

| 3,438,069 A | * | 4/1969 | Long | A47C 21/048 5/422 |
| 7,037,205 B1 | * | 5/2006 | Bowman | A47D 13/02 297/183.1 |

(Continued)

*Primary Examiner* — Rex R Holmes
(74) *Attorney, Agent, or Firm* — Nixon Peabody LLP; Ronald I. Eisenstein; Ravinderjit Braich

(57) ABSTRACT

Disclosed is a positioning device for use in a compound portable phototherapy device to contain and enhance therapeutic treatment to a subject. The positioning device comprises an inner surface composed of a non-porous, light reflective material, as well as an outer surface that may be opaque. Use of the positioning device in conjunction with a phototherapy device secures advantages of increased incident light directed on a subject and a controlled thermal environment for the subject. The positioning device may be portable and may be pliable, capable of being rolled or compressed. The positioning device may optionally include a visor, venting, and stabilizing cushioning. The positioning device may optionally include a thermal regulation element.

19 Claims, 3 Drawing Sheets

(52) U.S. Cl.
CPC ............... *A61N 2005/0663* (2013.01); *A61N 2005/0666* (2013.01); *A61N 2005/0667* (2013.01)

(58) Field of Classification Search
CPC .... A61N 2005/0667; A61N 2005/0652; A61N 2005/0662; A61F 7/08; A61F 7/0097
USPC .................................. 606/2–19; 607/86–94
See application file for complete search history.

(56) References Cited

U.S. PATENT DOCUMENTS

| | | | |
|---|---|---|---|
| 2004/0244301 A1* | 12/2004 | Dickson | B60N 2/28 52/3 |
| 2008/0094566 A1* | 4/2008 | Ishak | G02C 7/104 351/44 |
| 2008/0269844 A1* | 10/2008 | Logslett | A47D 15/00 607/88 |
| 2013/0111661 A1* | 5/2013 | Furuland | A47D 7/01 5/93.1 |
| 2014/0031906 A1* | 1/2014 | Brezinski | A61N 5/06 607/90 |
| 2016/0029813 A1* | 2/2016 | Kast | B60N 2/2845 280/30 |
| 2017/0172411 A1* | 6/2017 | Bloch-Salisbury | A61B 5/6892 |
| 2018/0299059 A1* | 10/2018 | McGoff | F16L 59/00 |

* cited by examiner

POSITIONING DEVICE FOR USE IN THERAPEUTIC TREATMENT

CROSS-REFERENCE TO RELATED APPLICATIONS

This application is a United States national stage filing under 35 U.S.C. § 371 of international (PCT) application no. PCT/US2016/040187, filed Jun. 29, 2016, and designating the US, which claims priority to U.S. provisional patent application No. 62/185,955, filed Jun. 29, 2015.

STATEMENT REGARDING FEDERALLY FUNDED RESEARCH

This invention was made with government support under grant R43 HD081745 awarded by the National Institutes of Health, and grant AID-OAA-F-14-00041 awarded by the United States Agency for International Development. The government has certain rights in the invention.

FIELD OF THE INVENTION

The invention is directed to a device capable of positioning a subject, which, when used in combination with a phototherapy device, facilitates and enhances therapeutic treatment, preferably therapeutic treatment involving electromagnetic radiation, such as phototherapy or thermotherapy in amounts sufficient to achieve a desired effect on the subject.

BACKGROUND OF THE INVENTION

Exposure to electromagnetic radiation has a wide variety of effects on subjects. Typically referred to as "photo-" or "light-" "treatment" or "photo-" or "light-" "therapy", a wide variety of devices and "treatments" (exposure regimes, or dosing) have been developed. Such treatments range from imaging, to germicidal, to tissue repair or growth, to treatment of a variety of diseases and disorders. The desired phototherapeutic effect is typically a result of the exposure properties of the electromagnetic radiation including, but not limited to, wavelength, intensity, duration, and frequency of exposure.

Examples of conditions for which phototherapy is considered useful for humans include, but are not limited to: tanning, wound repair, antiseptic treatment, acne, herpes, psoriasis, seasonal affective disorder (SAD), bulimia nervosa, sleep disorders, and skin cancer.

As a specific example, phototherapy has long been effective in the treatment of neonatal jaundice (hyperbilirubinemia). Jaundice is a common condition that affects 60% of term infants and more than 80% of preterm infants, i.e., an infant born before 37 week gestation. Hyperbilirubinemia, is caused by the excessive blood levels of bilirubin, a metabolite of hemoglobin. Bilirubin is a fat-soluble molecule that readily deposits in the skin, causing the yellow discoloration that is the hallmark of jaundiced infants.

Approximately 8% of all newborns develop severe hyperbilirubinemia, a condition where serum bilirubin levels exceed physiologic safety. Left untreated, infants with severe hyperbilirubinemia are at risk for neurotoxicity resulting in kernicterus, a form of permanent brain dysfunction, or death. Exposing the skin of a jaundiced newborn to certain types of blue light is effective in reducing blood bilirubin levels by converting bilirubin into water-soluble photo-isomers. These isomers are then eliminated without reliance on the immature conjugating function of the neonatal liver. Blue light phototherapy is typically required for only a few days, until the infant's liver can more efficiently bioprocess bilirubin.

Currently, most phototherapy is delivered in a neonatal intensive care units (NICU) or inpatient nurseries because effective, high-intensity devices are designed for those environments. The majority of commercially available, high intensity phototherapy devices are comprised of an array of LED lights or fluorescent bulbs that are positioned over an infant placed in a bassinet, radiant warmer, or in an isolette. Although LED fiber-optic pad or mattress type phototherapy devices, such as the BiliBlanket™ (Ohmeda Medical, Laurel, Md., as described in U.S. Pat. No. 5,339,223 to Kremenchugsky et al.) and Wallaby™ III (Respironics Inc., Pittsburgh, Pa.) are approved for treatment of infant jaundice in either hospital or home environments, such devices provide illumination to a limited body surface area. This renders them less effective than high intensity overhead phototherapy devices and unsuitable for treatment for severe hyperbilirubinemia. Additionally, these devices constrain the infant, and physically contact the infant, providing for reduced airflow and blood circulation.

Delivery of high intensity, overhead phototherapy to a jaundiced infant is complicated by several factors that necessitate treatment of the infant in a hospital. First, current overhead high-intensity phototherapy devices are not suitable for home use because infants must wear eye masks to protect from retinal photodamage that could result from exposure to the blue light. Infants must be under constant observation, typically with continuous monitoring of blood oxygen saturation due to risk of obstructing breathing by mask slippage over the newborn's nose and mouth. The eye mask also prevents the newborn's mother from viewing the face, creating a potential concern about the infant's wellbeing.

In addition, optimal treatment of the infant requires exposure of as much skin as possible to therapeutic light. The most common practice is for the infant to be undressed, except for the diaper and the eye mask, and placed in a plexiglass incubator. Placement of the undressed infant in an incubator provides a means of thermoregulation. Phototherapy lights are then positioned over the incubator, exposing the infant to treatment. When placed in the incubator, the infant is usually positioned under the light source without any physical boundaries, since these may interfere with light delivery. The consequence of this is that the infant will frequently move or "creep" away from the optimal position under the lights, reducing the efficacy of treatment. As a result, care providers must frequently reposition infants under phototherapy lights during treatment to achieve optimal therapy. Also, the lack of physical boundaries for a newborn is developmentally suboptimal, since newborns are frequently comforted by the sensation of being enclosed, such as by being held or by swaddling.

In addition to the above, another feature of overhead therapy that affects treatment efficacy is the limited exposure to light delivery at normal incidence to the skin. Overhead planar light arrays or spotlights do not distribute light evenly over the three-dimensional contour of the infant's body. As a result, the main area of exposure to light that is sufficiently therapeutic in on the chest and abdomen, with skin surface area on the sides of the body receiving little or no therapy. Since the total treatment time for an infant is correlated to the photodegradation of bilirubin, failing to maximize skin exposure results in longer hospital stays.

Published U.S. patent application no. 2004/0039428 describes a pad like device adapted to be placed over a phototherapy light source contains a medium that provides a comfortable support for a patient during phototherapy treatment and allows a portion of the light emitted by the light source to pass through the pad for phototherapy treatment. This device allows for radiation to be received by the subject from a source located below the device, thus the construct material allows for the transmittal of the targeting light waves. As a result of the light passing through the material the electromagnetic radiation received by the subject is a fraction of electromagnetic radiation transmitted. Additionally, the device is in direct contact with the subject, restricting air flow around the subject, as well as the subject's circulation. Furthermore, the device does not allow for the modulation of the ambient temperature surrounding the subject.

Published U.S. patent application no. 2008/0269844 describes a reflective crib liner for improving the efficacy of phototherapy is disclosed. The reflective crib liner has a fabric layer having dimensions to accommodate placement of the reflective crib liner in a bassinet used in a phototherapy treatment. The bassinet has at least one wall that defines an interior surface. A reflective layer is formed so as to cover at least a portion of the interior surface. The reflective layer has a first degree of reflectance with respect to visible light and a second degree of reflectance with respect to heat that is substantially lower than the first degree of reflectance. The reflective layer comprises a porous material having a light diffusing surface. Functionally, this device is not self-contained and requires the presence of a bassinet or isolette. Furthermore, this device does not embody a shielding component, and does not provide for temperature modulation of the subject.

Published U.S. patent application no. 2008/0116401 describes a garment that is substantially transparent to a predetermined range of wavelengths. The subject is placed in the garment and is then exposed for a period of time to a light source that includes light having all or a portion of the predetermined range of wavelengths. The garment consists of a blanket or hat that is made from a fabric that is substantially transparent to visible wavelengths. The subject is then exposed to electromagnetic radiation. A limitation of this device is that the subject is not secured in an optimal location for the receipt of the electromagnetic radiation. The device also is not self-contained, and requires the use of an isolette or bassinet. The subject is further required to wear a mask to prevent ocular damage. Furthermore, the device does not have the means for providing modulation of the ambient temperature of the subject.

Similarly, U.S. Pat. No. 8,756,731 describes a swaddling blanket for providing phototherapy to infants. This device has the same limitations as published U.S. patent application no. 2008/0116401, in that it requires the use of an isolette or bassinet, requires the subject to wear a mask to prevent ocular injury, and does not provide a mechanism for modulating the ambient temperature of the subject.

The present invention resolves these shortcomings. The present invention allows for the positioning of a subject in a desirable manner in relation to the phototherapy source in order to facilitate the application of a therapeutic treatment to the subject. The present invention is self-supporting and eliminates the need for a bassinet or incubator used during the application of therapeutic treatment. As such, the present invention may be used in remote areas, where access to hospitals and clinic is extremely limited, or in either the hospital or home when used with the Bili-Hut™ portable phototherapy device. Additionally, one or more of the sides of the present invention's inner surface is comprised of a reflective material, which provides for an increase in the reflection of external electromagnetic radiation upon the subject at normal incidence, improving skin penetration of light and therapeutic efficacy.

SUMMARY OF THE INVENTION

The present invention is directed to an enclosure or "positioning device" useful to position a subject in relation to the phototherapy source to enhance therapeutic treatment. Such treatment may comprise electromagnetic radiation therapy, such a phototherapy, or thermotherapy, although the present invention has utility for end users in any areas of their choosing or necessity.

The present invention is a positioning device that provides light amplification and increased skin exposure to optimize overhead phototherapy. In addition, the device may be adapted to incorporate protective shading or filtering from electromagnetic radiation, such as eye protection. The device may be adapted to incorporate heating elements, such as phase-change materials, to provide thermoregulation to the subject. The device also may be constructed with materials that reflect heat toward the subject, circumventing the need for and incubator for thermoregulation. The present invention is adaptable for use with existing overhead phototherapy devices, for example the BILI-HUT™ (Little Sparrows Technology, Winchester, Mass.; WO 2014/018103) and the Natus neoBLUE LED Phototherapy System™ (Natus Medical Inc., Pleasanton, Calif.) The present invention is of a construct to improve proper physical conformation and exposure of a subject to facilitate a desired therapeutic treatment, for example increase in the amount of electromagnetic radiation supplied to the subject. The present invention may be constructed of lightweight material and may be flattened, folded, compressed, or otherwise collapsed, to a size smaller than that of its operating size. The present invention may be adapted to provide thermal regulation of the subject.

The present invention is easy and inexpensive to manufacture, to transport, and to ship. The present invention requires no special facilities, equipment, power requirements, maintenance or training to assemble and to operate, thus making it particularly useful in areas of remote access and developing countries, where specific needs may be the greatest.

The positioning device of the present invention comprises a bottom side, a head side, a foot side, a right side, and a left side; said sides comprising an inner surface and an outer surface. Since the positioning device provides an enclosure for the patient, it allows for stabilization of the subject, allowing the subject to remain in an optimal location relative to the phototherapy lights in which to receive treatment. The positioning device is not limited in its size or shape, but is preferable adaptable for use in an overhead phototherapy devices such as the BILI-HUT™. The inner surface of at least one of the sides may be comprised of a light reflective material, providing the positioning device with the capability of reflecting light onto a subject from a light source located outside of the positioning device; the reflected light being of a sufficient intensity and wavelength to provide a desired therapeutic effect to a subject. The reflective material may be in the form of a removable liner.

As noted above, the positioning device of the present invention may be utilized in conjunction with overhead phototherapy devices. In one embodiment of the positioning device incorporates insulation material in the walls and undersurface and a receptacle for a heating element so that it may eliminate the need for phototherapy devices to be operated in concurrence with an expensive incubator for thermoregulation. Unlike incubators and isolettes, the positioning device provides for stabilization of the subject, allowing the subject to remain in an optimal location in relation to the phototherapy source in which to receive treatment. Another aspect of the positioning device which provides a benefit over incubators and isolettes is its portability, allowing for its use in multiple environments, for example hospitals, clinics, and homes.

In a preferred embodiment, a compound portable phototherapy device adapted for the treatment of hyperbilirubinemia is provided, comprising separable parts I and II, part I of said device comprising:

(a) a floor section essentially rectangular in shape defined by a head end and a foot end and two sides, said floor being dimensioned so as to support the length of a reclining infant of up to about five kilograms, said floor having a fold-over tab attached along at least a portion of one side of the floor, the tab exhibiting one or more fasteners along its length;

(b) a canopy section attached to said floor section along the side of the floor section opposite said fold-over tab, said canopy section extending from a proximal end attached to said floor section to a distal edge, said canopy section exhibiting one or more fasteners near its distal edge capable of mating with the corresponding fasteners on said fold-over tab to securely but reversibly join said distal edge of the canopy section to said fold-over tab, said canopy section being dimensioned such that joining said distal edge of the canopy section with the fold-over tab attached to said floor section forms an arcuate shell over said floor section, defining an assembled configuration having an inner surface facing said floor section and an outer surface;

(c) a plurality of light sources affixed to the inner surface of said shell, said plurality of light sources being capable of emitting light of a wavelength of 400-550 nm;

(d) an electrical power source;

(e) circuitry operably connecting said power source to said plurality of light sources; and (f) one or more frame support elements affixed to said canopy section which are flexible yet rigid enough to support said canopy section in an arcuate shell configuration; wherein the inner surface of said shell comprises a reflective surface; and wherein said floor section, fold-over tab, and canopy sections are of a pliable material such that, when said fasteners are not fastened, said floor section, tab, and canopy section, together with said affixed plurality of light sources and frame support elements are capable of being flattened or rolled or compressed to a disassembled size smaller than that of its operating size; part II of said device comprising:

(a) a compressible positioning device dimensioned to encompass an infant and dimensioned to fit within the enclosure of part I of said device, said positioning device having a floor and raised sides defining left and right sides, a foot end, and a head end, at least a portion of the inner surface of said positioning device comprising a reflective surface; and (b) optionally, affixed over the head end of said positioning device, a visor positioned so as to mask the eyes of an infant placed in said positioning device from light emitted from outside of the positioning device;

wherein said positioning device is capable of reflecting light onto said subject from a light source located outside of said positioning device; and wherein, in the assembled configuration, said plurality light sources is capable of transmitting light of sufficient intensity and wavelength to provide a desired phototherapeutic effect to an infant positioned in said positioning device which in turn is positioned on the floor section, without said plurality of light sources of part I of said device being in direct physical contact with said infant.

In one embodiment, the positioning device of the present invention is capable of being flattened, folded, rolled, compressed, or otherwise collapsed to a size that is less than the working space of the positioning device in its operational configuration. In one embodiment of the invention, the inner surface is comprised of a non-porous material. In a further embodiment, the, non-porous material comprises medical grade vinyl. In one aspect of the invention, the inner surface comprises a removable liner. In one embodiment of the current invention, at least one side of the positioning device comprises a vent. In another embodiment of the invention, at least one side of the inner surface further comprises stabilizing cushioning.

The outer surface of the present invention, as more fully disclosed and described herein, is not limited in its shape or composition of matter. In one aspect of the invention, the outside surface is non-reflective and may include handles or other positioning or transporting aids In one aspect of the invention, the positioning device comprises a visor, which may be permanently attached or may be removable. In one embodiment of the invention, the visor may be attached to the head of the positioning device. In another embodiment of the invention, the visor may be positioned to form a top side of the positioning device. In addition, the visor may be so constructed to be extended to an operating position or retractable. In one embodiment of the invention, the visor is semitransparent or contains a semitransparent window. In another embodiment of the invention, the semitransparent visor or window functions to selectively filter out electromagnetic radiation of a certain wavelength or range of wavelengths, for example, blue or ultraviolet light, such as light within a range of about 400 to about 550 nm. In a further embodiment of the invention, the visor may be detachable, using any number of attachment designs or devices known in the art.

In another embodiment, the visor may be partially lined with non-reflective material to further reduce light exposure to an infant's eyes. In this embodiment, the positioning device may also be constructed such that the area surrounding the infant's head is also lined with non-reflective material to further minimize harmful exposure of the eyes to light.

In one embodiment, the current invention may comprise a thermal element, such that the thermal element is capable of modulating the temperature inside the positioning device relative to the ambient temperature outside of the positioning device. In another embodiment, the thermal element is a heating element. In another embodiment, the thermal element is a cooling element. In a further embodiment, the thermal element comprises a thermostable gel.

In one embodiment, the positioning device is 16 to 26 inches in length, preferably 18 to 24 inches in length. In preferred embodiments, the positioning device is 19.5 to 22.5 inches in length. In a preferred embodiment, the positioning device is 21 inches in length.

In one embodiment, the positioning device is 9.25 to 5.25 in height. In preferred embodiments, the positioning device is 9.25 to 5.25 in height at the head/foot ends of the device, tapering to 6.75 to 2.75 inches at the center of the device. In preferred embodiments, the positing device is 7.25 inches in height at the head/foot ends, tapering to 4.75 inches at the center of the device.

In one embodiment, the positioning device is 16.25 to 10.25 inches in width at the widest point. In preferred embodiments, the positioning device is 14.75 to 11.75 inches in width at the widest point. In a preferred embodiment, the positioning device is 13.25 inches in width at the widest point.

Additional features of the present invention may include handles, fasteners, or snaps.

As more fully disclosed and described herein, the positioning device of the present invention may be used in combination with a phototherapy source to treat a variety of subjects to achieve a desired therapeutic effect, such as a phototherapeutic effect and a thermotherapeutic effect. The positioning device may be used in combination with a phototherapy source or device to treat a variety of diseases and disorders responsive to electromagnetic radiation, such as hyperbilirubinemia, psoriasis, acne, wound healing, and seasonal affective disorder.

The phototherapy device to be used in conjunction with the positioning device described herein minimally comprises a light source, circuitry, a shell, and a power source. The light source is operably connected to the power source through the provided circuitry, and is attached to the shell. The light source is positioned on the inner surface of the shell and is capable of transmitting light of sufficient intensity and wavelength to provide a desired phototherapeutic effect to a subject placed under the arc of the shell without being in direct physical contact with the subject. The phototherapy device and the positioning device described herein may be used in conjunction with each other to position the light source and a subject relative to each other such that the exposure of the subject to the transmitting light of the phototherapy device is maximized, the quality of the exposure to phototherapeutic light is optimized (e.g., in terms of incident angle of light impinging on the skin of a subject), the efficiency and efficacy of the phototherapy are maximized, and the desired phototherapeutic effect is achieved in an acceptable period of time, e.g., the coordinated use of the devices potentially allows for shorter treatment times.

In a preferred embodiment, the positioning device is designed for use in conjunction with the BILI-HUT™ portable phototherapy device (WO 2014/018103) used for the treatment of hyperbilirubinemia in newborns or other portable light-emitting device capable of delivering electromagnetic radiation (EMR) to a subject in an amount, and of a wavelength sufficient to achieve a desired effect in the subject.

The positioning device, when used with the BILI-HUT™ portable phototherapy device, by virtue of its minimal size and weight as well as its ability to provide thermal ambient modulation, eliminates the need for inpatient phototherapy treatment, allowing phototherapy treatment to take place in the newborn's home, or in other non-hospital locations. Additionally, the current example provides for about 40% more light exposure to the newborn than would be received without the positioning device, as a result of the highly reflective inner surface.

DETAILED DESCRIPTION OF THE INVENTION

Figure 1:
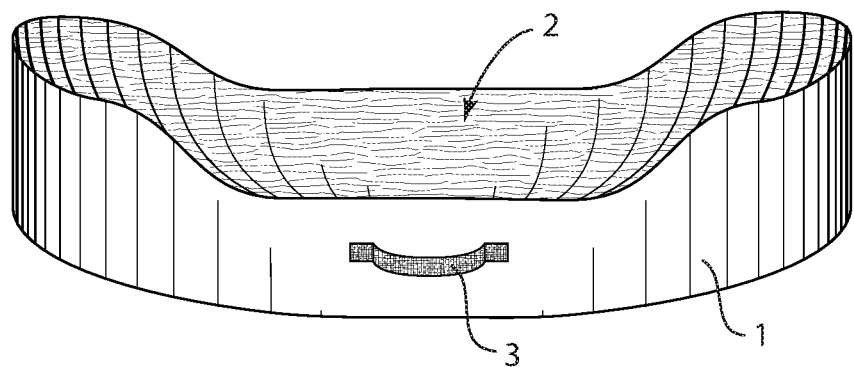
FIG. 1 is a side view of an embodiment of the assembled positioning device (1) of the invention. Identified within the figure are a reflective inner surface (2) and a handle (3).
Figure 2:
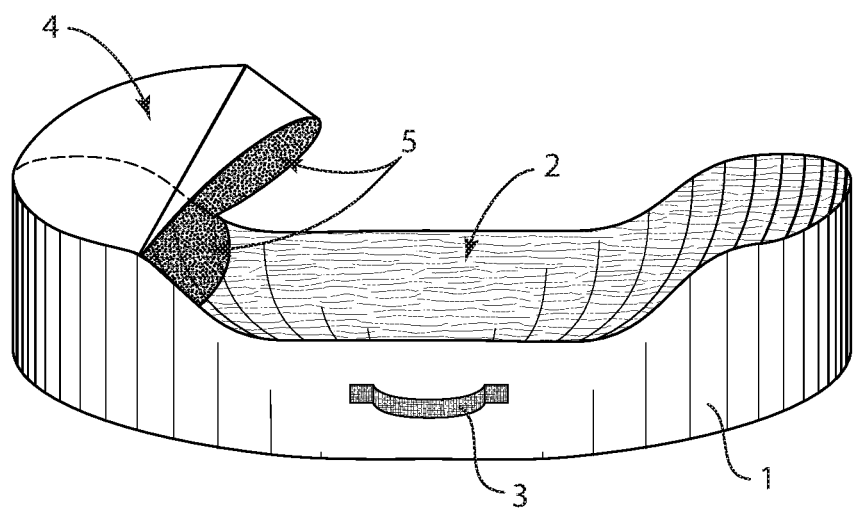
FIG. 2 is a side view of an embodiment of the assembled positioning device (1). Identified within the figure are a reflective inner surface (2), a handle (3) a visor (4), and a non-reflective inner surface (5).
Figure 3:
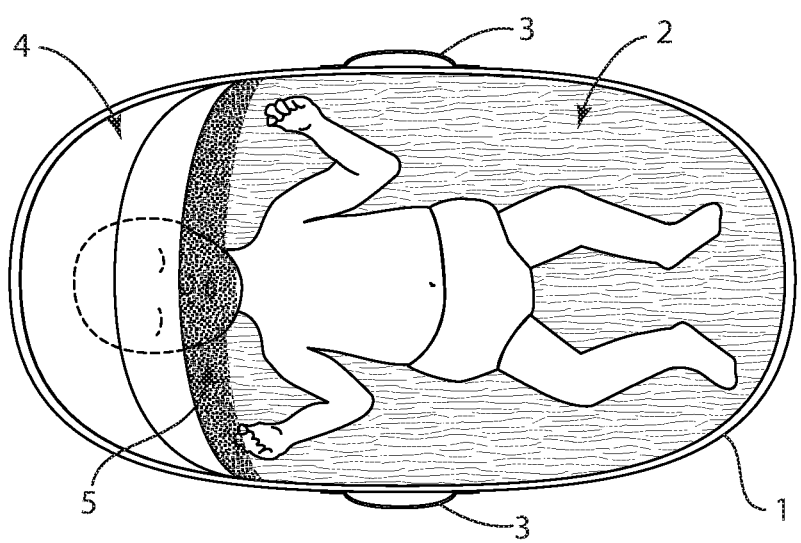
FIG. 3 is an overhead view of an embodiment of an assembled positioning device (1). Identified within the figure are a reflective inner surface (2), a handle (3), a visor (4), and a non-reflective inner surface (5).
Figure 4:
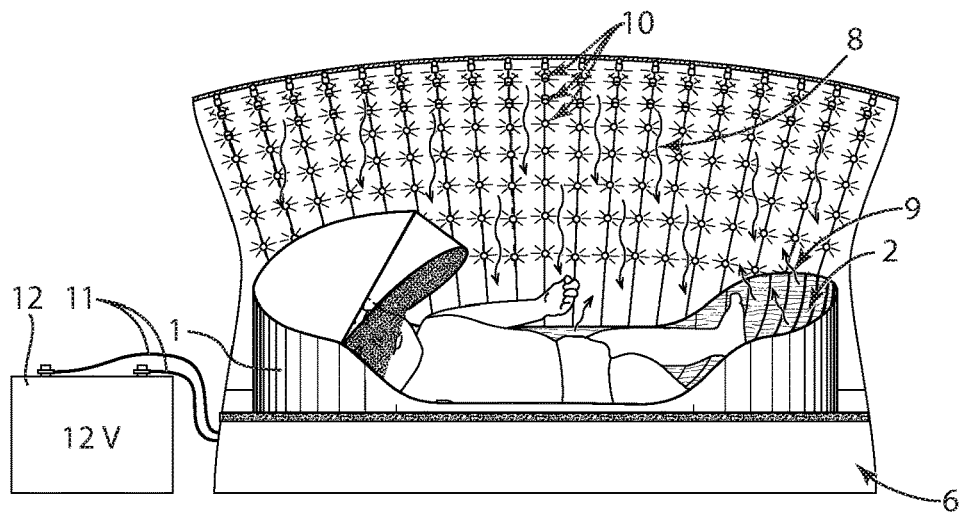
FIG. 4 is a perspective view of an embodiment of an assembled positioning device (1) in operation with a portable phototherapy apparatus (6). Identified within the figure are a reflective inner surface (2), a plurality of light-emitting diodes (LEDs) comprising the light source (10), a power source (12), circuitry (11) electromagnetic radiation (8), and reflected electromagnetic radiation (9). The power source (12) and circuitry (11) are omitted from the other illustrations but will be understood as being present when the apparatus is in operation.
Figure 5:
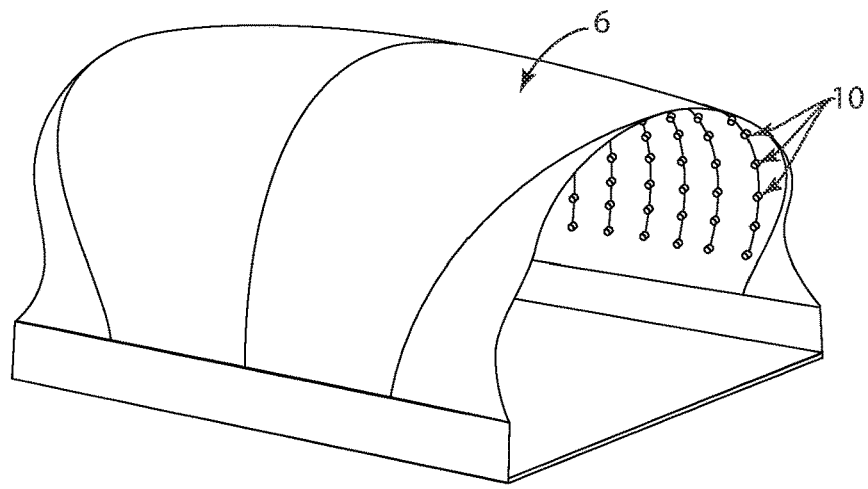
FIG. 5 is a perspective view of an assembled portable phototherapy apparatus (6) in conjunction with which the assembled positioning device may be used, to position the subject advantageously with respect to the emitting light and to enhance the phototherapy treatment. Identified within the figure are a portable phototherapy apparatus (6) and a plurality of light-emitting diodes (LEDs) comprising the light source (10).

As used herein, "position", "encompass", or "contain" refers to the ability to surround or to hold within a device or structure. Specifically, the positioning device of the present invention is constructed to encompass a subject relative to the phototherapy source such that the subject is contained within the positioning device to hinder the subject from moving outside of the positioning device, but without unduly constraining or restricting movement of the subject. "Encompass" also pertains to a height element, specifically, the height of the sides of the positioning device are sufficient to restrict movements by the subject that would significantly decrease exposure to therapeutic radiation; in preferred embodiments, the height of the sides will be equal to or greater than the height of the subject when placed within the positioning device.

As used herein, "subject" is any object or individual desired to be exposed to therapeutic irradiation. A subject as referenced herein may be a nonliving instrument, surface, material, or substance, or a subject may be a living biological sample or organism, including human infants. For embodiments relating to treatment for hyperbilirubinemia, the typical subject will be a newborn human infant exhibiting jaundice of up to about five kilograms and up to about 27 inches or so in length.

In the following detailed description of the various embodiments of the invention, numerous specific details are set forth in order to provide a thorough understanding of the various embodiments of the invention. However, one or more embodiments of the invention may be practiced without these specific details. It is to be understood that other embodiments may be utilized and structural changes may be made without departing from the scope of the present invention.

Provided herein is a positioning device capable of encompassing a subject and positioning a subject in relation to the phototherapy source for the purpose of reflecting electromagnetic radiation onto the subject from an external light source in sufficient intensity and wavelength to provide a desired therapeutic effect. The positioning device is inexpensive and easy to manufacture, to transport, to ship and to use. The positioning device has ultimate utility for end users in areas of their choosing or necessity.

I. The Sides

As used herein, "side" has the plain meaning as understood by a person of ordinary skill in the art. "Side" refers to one of the surfaces forming the boundary of the positioning device. A "side" may be integral with other sides, or may be a separate element from other sides.

The positioning device of the present invention comprises a shallow receptacle resembling a tray or basket, having a floor and elevated sides defining partially enclosed space, open above but bounded by the sides. The shape of the positioning device is advantageously elongated to accommodate a human infant placed lengthwise on the floor of the device. The shape will be defined by the floor section and may be rectangular, in which case there will be four sides elevating from the floor, i.e., left and right sides, a head end, and a foot end. Alternatively the shape of the positioning device may be oval, in which case the sides will form a continuous wall (without corners) running around the entire edge of the floor of the positioning device. Numerous equivalent shapes can be substituted without altering any aspect of the function of the positioning device. One end of the positioning device of whatever shape will be designated the head end to correspond to the end at which an infant's head will be placed when the device is used in the treatment of an infant subject. The designation of one end as the head end automatically defines the right and left sides and the foot end. The floor and sides define an inner surface and an outer surface. The inner surface of the floor is designed to be the side upon which the subject rests, and is the side to which the sides/ends are attached.

As used herein, the term "partial side" refers to a side in which its height is less than the height of the tallest side of the device. Conversely, the term "extended side" refers to a side in which its height is greater than the height of the shortest side of the device.

The sides of the positioning device are not limited by their size, shape, construction, or composition of matter. The function of the sides is multifold. The sides may serve to encompass the subject within the positioning device. The sides may also assist in the modulation of the ambient temperature within the positioning device. In one embodiment of the invention, the sides comprise an insert to the inner surface of the positioning device, the purpose of which is to stabilize the subject.

In one embodiment, the present invention comprises a floor, a head end, a foot end, a left side and a right side. The labeling of the sides is arbitrary, with the exception of the floor, which is the side to which the other sides are connected or attached. In one aspect of the invention, the head end is extended, and may contain, or have mounted to it, a visor. In another aspect of the invention, one or more sides may be partial, to allow for the ease of insertion and removal of a subject to the interior of the positioning device. In another embodiment, one or more of the sides may comprise vents, for assisting in the modulation of the ambient temperature of the positioning device via airflow regulation.

In one embodiment of the invention, the sides are continuous. In another embodiment of the invention, one or more of the sides may be collapsible and/or detachable from the positioning device. In another aspect, the sides may be components of a single construct. The sides comprise an inner surface of the positioning device, an outer surface of the positioning device and any number of layers or pockets. For example, one side of the positioning device may contain a pocket suitable for the placement of a thermal element, such as a heating element or an insulating material.

The size and shape of the sides may be customized for any number of applications. For example, the positioning device may be fitted to a pre-existing phototherapy device. The sides may further comprise any number and variety of fasteners, channels, sheaths, loops, buttons, weights and the like. The sides may take on any number of shapes, including but not limited to planar, multifaceted, arched, tubular, or otherwise, and may comprise any number of support structures, such as fiberglass rods. The sides may be composed of any number of materials, such as fabrics, plastics, fibers, or cloth.

II. The Inner Surface of the Positioning Device

As used herein, "inner surface" refers to the inner surface bordered by the floor and elevated sides/ends of the positioning device.

The inner surface of the positioning device is not limited by its size, shape, construction, or composition of matter, and is generally defined by the size and shape of the sides. The purpose of the inner surface is to encompass a subject. In one embodiment, the inner surface may partially or fully comprise a reflective surface, reflecting electromagnetic radiation delivered from an outside source onto a subject placed within the positioning device in order to provide or increase a desired therapeutic effect to the subject. In another embodiment, the inner surface may partially or fully comprise a non-reflective surface, for example to minimize reflection of light to the subject's eyes. The inner surface may also assist the positioning device in regulating the ambient thermal properties of the interior of the positioning device.

In one embodiment of the invention, the inner surface comprises a bright white light-reflective material. The inner surface may further comprise a non-porous material. The inner surface may comprise the sum of the inner surfaces of the sides, or alternately, the inner surface may comprise a removable liner.

The inner surface may be composed of any number of materials, such as fabrics, plastics, fibers, or cloth, selected to conform to medical standards and possess the necessary properties to enhance the irradiance. In one embodiment of the invention, the inner surface comprises a material with a mesh-like backing with a polyvinyl chloride coating, providing the inner surface with high reflectivity and antifungal and antibacterial properties. In one embodiment, the interior of the positioning device may be concave in shape. Further, the inner surface may comprise any number and variety of fasteners, buttons, holes, elastic bands, and the like to facilitate the attachment of the inner surface to the sides of the positioning device.

III. The Outer Surface

As used herein, "outer surface" refers to the outer surface of one or more of the sides of the structure.

The outer surface of the positioning device is not limited by its size, shape, construction, or composition of matter, and is generally defined by the size and shape of the sides. The purpose of the outer surface is to provide support to the positioning device. The outer surface may also assist in the regulation of the ambient thermal properties of the positioning device.

As used herein, "absorptive" refers to the ability to absorb light and/or heat.

In one embodiment of the invention, the outer surface comprises absorptive material. The outer surface may comprise the sum of the outer surfaces of the sides, or alternately, the outer surface may comprise a removable liner.

The outer surface may be composed of any number of materials, such as fabrics, plastics, fibers, or clothes. In one embodiment of the invention, the outer surface may comprise any number and variety of fasteners, buttons, holes, elastic bands, and the like to facilitate the attachment of the outer surface to the sides of the positioning device.

IV. The Visor

In one embodiment, the positioning device of the present invention further comprises a visor.

As used herein, "visor" refers to a surface that protects one or more areas of the subject, such as by shielding the protected area(s) of the subject from electromagnetic radiation such as light. Alternatively, the visor may filter particular wavelengths of electromagnetic radiation from the protected area of the subject, typically the head or more specifically the eyes of the subject. As such, the visor may be transparent, semi-transparent, or opaque. As used herein, "light" refers to electromagnetic radiation of varying wavelengths as understood by persons of ordinary skill in the art.

The visor of the positioning device is not limited by its size, shape, construction, or composition of matter. The function of the visor is to shield one or more portions of the subject from the externally sourced electromagnetic radiation. Preferably, the ocular region of the subject may be shielded. The visor may additionally serve to aid in the modulation of the ambient temperature within the positioning device.

As used herein, "attached" has the plain meaning as understood by a person of ordinary skill in the art. "Attached" refers to any type or form of connection of one component to another. The connection may be permanent or detachable.

In one embodiment of the invention, the visor may be attached to one or more sides of the positioning device. In another embodiment of the invention, the visor may be attached to the head end/side of the positioning device. The visor may be integrated into one or more sides in such a manner as to be an extension of the side(s). The visor may be retractable, and may be supported by a flexible, non-compressible rod which will serve to ensure that the visor may not be collapsed to come into direct physical contact with the subject.

In one embodiment, the visor may be semi-transparent and may be composed of any number of plastics, fibers, or cloth. Suitable semi-transparent visor material may include welding shield material available from manufactures such as 3M Occupational Health and Environmental Safety Division (St. Paul, Minn., USA). Alternately, the visor may be opaque, blocking all light from the portions of the subject shielded by the visor.

V. The Thermal Unit

In one embodiment, the present invention may contain a thermal unit. As used herein, "thermal unit" refers to any number of devices known to persons of skill in the art, which devices are capable of regulating the ambient temperature within the positioning device. A "thermal unit" may be a warming unit, or a cooling unit, or a unit which serves to maintain the temperature within the positioning device within a pre-determined temperature range. The "thermal unit" may be powered or non-powered. The thermal unit may be permanently incorporated in to the positioning device or may be removable.

In one embodiment of the invention, the thermal unit may be placed contiguously to one or more of the sides of the positioning device. In another embodiment of the invention, the thermal unit may be embedded within one or more of the sides.

In one embodiment of the invention, the thermal unit may consist of a thermostable gel. In another embodiment of the invention, the thermal unit may consist of a heating pad or a heating blanket. In another embodiment, the thermal unit is a cooling unit.

VI. The Phototherapy Device

As previously discussed, the phototherapy device to be used in conjunction with the positioning device described herein minimally comprises a light source, circuitry, a shell, and a power source. The light source is operably connected to the power source through the provided circuitry, and is attached to the shell. The light source is arrayed on the inner surface of the shell and is capable of transmitting light of sufficient intensity and wavelength to provide a desired phototherapeutic effect to a subject positioned under the shell, without being in direct physical contact with the subject. The phototherapy device and the positioning device described herein may be used in conjunction with each other to position the light source and a subject relative to each other such that the exposure of the subject to the transmitting light of the phototherapy device is maximized, the quality of the exposure to phototherapeutic light is optimized (e.g., in terms of incident angle of light impinging on the skin of a subject), the efficiency and efficacy of the phototherapy are maximized, and the desired phototherapeutic effect is achieved in an acceptable period of time, e.g., the coordinated use of the devices potentially allows for shorter treatment times.

Preferably, the design and construction of the phototherapy device is such that it is easily assembled (and disassembled) and operated by anyone with little or no technical expertise or training. Once assembled to its operational configuration, the method for use (treatment) of the phototherapy device comprises utilizing the positioning device to position the subject in the phototherapy device relative to each other such that the subject is capable of being exposed to the transmitting light of the phototherapy device, then exposing the subject to said transmitting light for a sufficient duration to achieve a desired phototherapeutic effect. In preferred embodiments, the utilization of the positioning device within the phototherapy device achieves whole body exposure to the irradiance, e.g., head-to-toe exposure to the irradiance. In embodiments of the positioning device incorporating a visor, preferably the head region of the subject is at least partially shielded from the irradiance, and most preferably the ocular region is shielded from the irradiance.

VI(A). The Light Source

The light source of the phototherapy device is not limited in its composition, construction, or operation, but refers to any source capable of emitting a detectable amount of electromagnetic radiation (EMR) of any range or specificity of wavelength. As used herein, the terms "light", "light source", "phototherapy" and the like, are not limited in the wavelength of EMR emission, but encompass the full EMR spectrum, including what are commonly classified as; radio waves, microwaves, infrared light, visible light, ultraviolet light (e.g., UVA, UVB, UVC), X-rays, and gamma rays (static electricity and sound waves are not EMR). The light source may emit EMR of a single wavelength or any range of wavelengths. Similarly, the light source, and EMR emitted therefrom, is not limited in its intensity or duration of transmission. The light source may be active for continuous EMR transmission, intermittent EMR transmission, pulsed EMR transmission, or EMR transmission for a specified duration. Such intensity, frequency, and duration may be an intrinsic property of the light source, or may be further set or controlled by the circuitry of the phototherapy device.

The desired EMR transmission and light source are selected depending on the desired phototherapeutic effect the practitioner wishes to obtain. For example, UVA is known to be useful for phototherapy of psoriasis (in conjunction with photoactive agents). UVB is a DNA-damaging EMR, and is known to be useful for sterilization (e.g., germicidal), tanning, and the treatment for psoriasis. UVC is known to be useful for sterilization, including wound treatment. Light sources emitting EMR in the range of about 400 to about 550 nm are useful for treating jaundice. Light sources emitting EMR in the range of about 405 to about 420 nm are useful for treating acne. Light sources emitting EMR in the range of about 465 to about 490 nm are useful for various circadian rhythm and sleep disorders. Light sources emitting EMR in the range of about 660 are useful for wound repair. Effective wavelengths cited herein may vary plus or minus 15%.

The light source is not limited in number. The light source may comprise a single point source of light, or may comprise a plurality of light sources. In one embodiment such plurality of light sources are distributed (evenly, uniform, non-uniform, or randomly) along a surface (e.g., inner surface), or portion of a surface of the shell. A variety of light sources are known and used in the art. Such light sources include, but are not limited to incandescent, fluorescent, laser, halogen, xenon, metal-halide, fiber optics, and light emitting diodes (LEDs; including organic light emitting diodes, OLEDs, and polymer light emitting diodes, PLEDs). Optionally, the light source may further comprise a filter to adjust or to narrow the wavelength of emitted EMR. The number of light strips required for a therapeutic level of light is determined by the total irradiance of the light source, as this may vary by manufacturer, the distance of the angle of light dispersion, the distance from the subject, and the reflectivity of the shell material.

In one embodiment, the light source is a plurality of LEDs. LEDs, and LED strings (or other arrays) are well known and commercially available (e.g., CREE, Inc., 4600 Silicon Drive, Durhanl, N.C. 27703; Nichia America Corporation, 3775 Hempland Road, Mountville, Pa. 17554). LEDs and LED arrays emit high intensity light at a low temperature, are inexpensive, lightweight, flexible, and may be selected based upon a wide variety of specific light wavelengths ("colors"); e.g., ~400 nm (violet light), ~475 nm (blue light), ~510 nm (green light), ~570 nm (yellow light), and ~650 nm (red light). LEDs that emit red light are useful for treating herpes. LEDs that emit white or yellow light are useful for treating SAD. LEDs that emit ultraviolet light are useful for treating psoriasis. LEDs that emit blue light are useful for treating jaundice, also known as hyperbilirubinemia. LEDS that emit blue light with a range of about 400 to about 550 nm are particularly useful. LEDS that emit blue light of about 450 to about 470 nm are preferred, as this is the range of light of peak absorption for bilirubin.

VI(B). The Power Source

The power source of the phototherapy device is not limited in its design, construction, or output, but refers to any source capable of providing useable energy of a sufficient quality and quantity (e.g., voltage, wattage, amperage, resistance) to the light source of the phototherapy device such that the light source emits a detectable amount of EMR. Typically, the power source is electric in nature and may be provided as either Alternating Current (AC) or Direct Current (DC), or some combination/transformation of both.

In one embodiment, the power source is line power. Line power, as is known in the art, generally refers to electricity distributed and provided as a service from a larger electricity generating source (e.g., "household power", "outlet electricity", "grid power", and the like). In another embodiment, the power source maybe any of a number of generators, including but not limited to, a biogas generator or a thermo-electric generator. In another embodiment, the power source is from one or more batteries or fuel cells. The battery power source may be rechargeable or disposable. Any of the wide array of batteries known in the art may be useful as a power source, including but not limited to dry cell, wet cell, alkaline, lithium, lithium-ion, lead-acid, and nickel-cadmium. In one embodiment the battery is a 12 volt battery. In one embodiment, the power source is photovoltaic in nature.

VI(C). The Circuitry

The circuitry of the phototherapy device is not limited in its design or construction, but refers to any operable means of transmitting useable energy from the power source to the light source. Typically, such circuitry utilizes wire capable of conducting electricity.

In various embodiments, the circuitry may further comprise various regulating and controlling devices, including but not limited to switches, timers, rheostats, potentiometers, transformers, resistors, capacitors, sensors, data recorders, and any number and variety of specialized integrated circuits and components known in the art. In one embodiment, the circuitry further comprises over-voltage and/or short-circuit protection. The phototherapy device is not limited in design or placement of the various circuitry components. In some embodiments, circuitry components may be positioned close to the light source (e.g., to monitor or control the light source). In other embodiments, various circuitry components may be positioned along a surface of the shell (e.g., to monitor or control the local environment of the phototherapy device). In other embodiments, various circuitry components may be positioned close to the power source (e.g., to improve the portability of the phototherapy device).

VI(D). The Shell ("Canopy")

For purposes of this disclosure, "shell" and "canopy" are used interchangeably. The shell of the phototherapy device is not limited in its size, shape, or composition of matter. Importantly, the shell is capable of being flattened, folded, rolled, compressed, or otherwise collapsed, to a size that is less than the working space of the assembled and operational phototherapy device. The shell, therefore, may be composed of two or more rigid panels that can articulate, or can otherwise be attached one to another such that they can be configured (e.g., "assembled") to form the structure of the phototherapy device, and can be alternatively configured (e.g., folded, or "disassembled") for easy transport or storage when not in use. In an alternative embodiment, the shell may be composed of a number of semi-rigid, pliable, or fabric materials, which material may be flattened, folded, rolled, compressed, or otherwise collapsed, to a size that is less than the working space of the assembled and operational phototherapy device. In one embodiment, the shell may be composed of any of a number of textiles, fabrics, or cloths known in the art. MYLAR is one fabric of particular utility in constructing the shell. One such example is "Grow tent reflective canvas" provided by Rogue Hydroponics (Hamden, Conn.).

The shell may possess any one or more physical characteristics that may provide additional benefit to the phototherapy device of the present invention, for example, to reduce, or to augment, environmental stimuli. In one embodiment, the shell may possess a reflective surface. Such a reflective surface, appropriately positioned relative to the light source serves to redirect transmission of EMR to the subject. The shell may be so constructed or fabricated such that the light source and/or circuitry is integrated into the shell (see, e.g., U.S. Pat. No. 7,274,844). The shell may be translucent, to permit light (or viewing) through the shell, or the shell may be opaque, to prevent light (or viewing) through the shell. In some embodiments, the shell may contain a transparent or semi-transparent window or opening to allow for viewing inside the shell or manipulation of subjects or articles within the shell. The shell may further provide a surface (e.g., a transparent plastic layer), protective of staining, bodily fluids, cleaning solutions and the like. The shell may further provide sound deadening features to the phototherapy device.

The size and shape of the shell may be customized for any number of applications. For example, the shell may be fitted to conform to a pre-existing structure, such as an isolette, crib or bed (e.g., in the instance of phototherapy for infants). The shell may be fitted to conform to an aquarium or terrarium (e.g., in the instance of phototherapy for other animals or plants). The shell may be designed similar to, or modified from, any number of tent designs (e.g., in the instance of phototherapy for larger subjects, such as tanning devices for humans). The shell may further comprise any number and variety of retaining channels or sheaths, loops, clasps, hooks, buttons, holes, weights and the like to facilitate attachment of the phototherapy device to a pre-existing structure or otherwise immobilize the phototherapy device. The shell of the phototherapy device may take any of a variety of shapes, including but not limited to planar (panels), multi-faceted, conical, arched, tubular, or otherwise cylindrical or semi-cylindrical in shape.

VI(E). The Frame Support

In one embodiment, the phototherapy device further comprises a frame support. Such frame support is not limited in its composition, size or shape, but, importantly, is flexible, semi-rigid to rigid enough to support the phototherapy shell in a "free-standing" configuration. Similar to the shell, to maintain the portable feature of the phototherapy device, the frame support is capable of being flattened, folded, rolled, compressed, or otherwise collapsed, to a size that is less than the working space of the assembled and operational phototherapy device. In one embodiment, the frame support may be composed of two or more poles, rods, tubes, slats, springs, or the like that can articulate, or can otherwise be positioned one to another such that they can be configured (e.g., "assembled"), with the shell, to form the structure of the phototherapy device, and can be alternatively configured (e.g., folded, or "disassembled") for easy transport or storage when not in use. In an alternative embodiment, the frame support may be composed of one or more poles, rods, tubes, slats, springs, wire or the like that are capable of being flattened, folded, rolled, compressed, or otherwise collapsed, to a size that is less than the working space of the assembled and operational phototherapy device. As earlier discussed, the shell and frame support may be designed similar to, or modified from, any number of tent designs known in the art. In one aspect, the frame support comprises one of more flexible rods. In various embodiments, the frame support may be attached to the shell. The attachment may be of a permanent nature or may be designed to be removable, i.e., attachable (or inserted) and detachable, using any number of attachment designs and devices known in the art. For example, non-conductive, extruded fiberglass rods (¼" or ⅜" diameter) are widely available, and may be cut to suitable lengths for any particular shell shape or design.

In a preferred embodiment, the positioning device of the present invention is designed for use in conjunction with the BILI-HUT™ portable phototherapy device (WO 2014/018103) used for the treatment of hyperbilirubinemia in newborns or other portable light-emitting device capable of delivering electromagnetic radiation (EMR) to a subject in an amount, and of a wavelength sufficient to achieve a desired effect in the subject.

The positioning device, when used with the BILI-HUT™ portable phototherapy device, by virtue of its minimal size and weight as well as its ability to provide thermal ambient modulation, eliminates the need for inpatient phototherapy treatment, allowing phototherapy treatment to take place in the newborn's home, or in other non-hospital locations. Additionally, the current example provides for about 40% more light exposure to the newborn than would be received without the positioning device, as a result of the highly reflective inner surface and slightly concave shape of the interior of the positioning device.

The present invention is further illustrated by the following non-limiting examples.

Example 1

Construction of the Positioning Device

The non-limiting positioning device herein exemplified was designed for use in conjunction with the BILI-HUT™ portable phototherapy device (see, WO 2014/018103) used for the treatment of hyperbilirubinemia in newborns. The positioning device may of course be used with other portable light-emitting devices capable of delivering electromagnetic radiation (EMR) to a subject in an amount, and of a wavelength sufficient to achieve a desired effect in the subject. The positioning device constructed as described fits entirely within the BILI-HUT™ portable phototherapy device, thus providing a means to deliver head-to-toe irradiation to a subject placed in the positioning device which is, in turn, placed within the portable phototherapy device.

This invention, when used with the BILI-HUT™ portable phototherapy device, by virtue of its minimal size and weight as well as its ability to provide thermal ambient modulation, eliminates the need for in-patient phototherapy treatment, allowing phototherapy treatment to take place in the newborn's home, or in other non-hospital locations. Additionally, the current example provides for about 40% more light exposure to the newborn than would be received without the positioning device, as a result of the highly reflective inner surface and slightly concave shape of the interior of the positioning device.

The head end and the foot end of the positioning device, being extended sides (higher than the lateral sides), aid in the prevention of light leakage from the enclosure. Additionally, the fit of the positioning device inside the BILI-HUT™ provides for thermal regulation of the newborn.

This specific embodiment of the positioning device comprises the following elements and features:
  A. Flexible, reflective material
  B. Flexible, non-reflective material
  C. Foam insulation material
  D. Fabric thread (natural or synthetic)
  E. Fabric webbing or other material suitable for constructing handles.

Relationship Between the Components

The flexible, reflective material (A) was cut into an elliptical shape of a length of 21 inches×13.25 inches. This shape represents the inner surface of the floor. In the current example, this material was a mesh-like backing with a polyvinyl chloride coating, known in the industry as medical grade vinyl. It is commercially available from Spradling International, Inc. (Pelham, Ala., USA). The thickness of the floor material is 40 gauge.

The flexible, non-reflective material (B) was cut into an elliptical shape of a length of 21 inches×13.25 inches. This shape represents the outer surface of the bottom side (floor). In the current example, this material is also medical grade vinyl. The thickness of this material is 30 gauge.

The foam insulation material (C) was cut into an elliptical shape of a length of 20 inches×12.25 inches. This material represents a layer of insulation disposed between the inner surface of the floor and the outer surface (bottom) of the device. The thickness of this foam material is ½ inch.

The three elliptical pieces of material above were assembled and the perimeter was sealed using fabric thread (D). Alternatively adhesives or any of a variety of heat sealers may be used.

The flexible, non-reflective material (B) was cut into a strip of a sufficient length to rest on the perimeter of the bottom side created above. This strip represents the outer surface of the continuous head, right, foot, and left sides of the positioning device. The width of the strip (which will form the sides) was varied to provide sides of varying height when assembled. The width started at 4.75 inches, formed an arc that peaks at 7.25 inches, and returned back down to 4.75 inches, then formed a second arc that peaks at 7.25 inches, and returns back down to 4.75 inches. The contours of the strip, when assembled on the perimeter of the 3-layer floor section described above formed raised sides around the floor which are elevated to 7.25 inches at the head end and foot end and which are lower (4.75 inches) on the right and left sides.

The flexible, reflective material (A) was cut into a strip sufficient to cover the inner surface of the continuous head, right, foot, and left sides of the positioning device.

The foam insulation material (C) was cut into a strip of sufficient length and height to serve as insulation between the outer and inner surfaces of the continuous head, right, foot, and left sides of the positioning device.

The three pieces of material mentioned above, forming the continuous head side, right side, foot side, and left side were assembled, sealing the perimeters with either thread (D) or a heat sealer. The start of the head side is connected with the end of the left side, forming an ellipse, and the continuous strip for forming the sides was placed such that the bottom of the strip rested firmly on the floor section, which parts were stitched together using fabric thread.

Example 2

Positioning Device in Operation with Phototherapy Device

The positioning device of this example was designed for use in conjunction with the BILI-HUT™ (Little Sparrows Technologies, Winchester, Mass., USA) portable phototherapy device (WO 2014/018103) useful for the treatment of hyperbilirubinemia in newborns. The positioning device may be adapted for use with other portable light-emitting device capable of delivering electromagnetic radiation (EMR) to a subject in an amount, and of a wavelength sufficient to achieve a desired effect in the subject.

Figure 6:
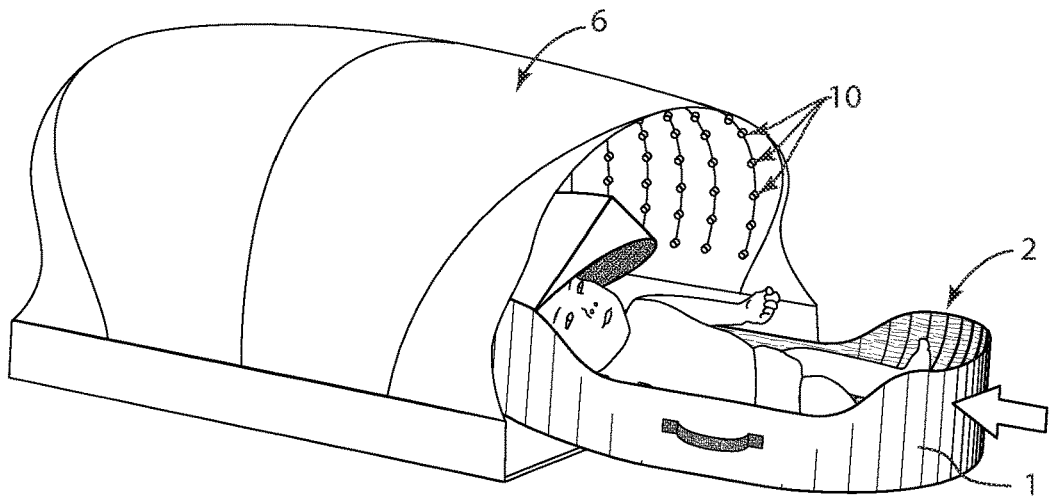
FIG. 6 is a perspective side angle view of an embodiment of an assembled positioning device (1) used in conjunction with an assembled portable phototherapy apparatus (6). Identified within the figure are a reflective inner surface (2) and a plurality of light-emitting diodes (LEDs) comprising the light source (10).

Treatment for newborns diagnosed with hyperbilirubinemia comprises placing the newborn in the positioning device and inserting the positioning device into the BILI-HUT™ portable phototherapy device so as to position the subject in relation to the phototherapy light source, in this case a plurality of light emitting diodes emitting blue light, arrayed in strips on the inner surface of an arcuate canopy, to allow maximum, uniform light exposure to a subject placed inside the positioning device. When a visor is in use, the newborn's head is placed under the visor at the head end of the positioning device and the newborn's feet are placed toward the foot end of the positioning device. The positioning device is inserted in the BILI-HUT™ phototherapy device (see FIG. 6) so that the newborn is fully encompassed within the phototherapy device, i.e., head-to-toe envelopment.

In testing with a model of a newborn baby, irradiance over anterior and lateral aspects of the newborn model were measured, calculated and normalized. Irradiance measurements were made using a commercial dosimeter (Biliblanket Light Meter II, GE Healthcare, United Kingdom) at 17 sites representing significant skin areas on an infant model. Values corresponding the measurements were placed on two grids of one inch squares. The first grid represented the profile of the infant when viewed anteriorly. The second grid represented the lateral view. Grid squares corresponding to skin area between measured values were filled with values of the closest reading with similar incidence angle. The irradiance over anterior and lateral aspects was summed, then normalized to the irradiance of a planar LED light array without positioning insert.

This experiment was performed with the same flexible light array (i.e., from a BILI-HUT™ device), positioned above the model infant in a planar configuration and then positioned above the model infant an arcuate (arched) configuration (that is, the arched canopy configuration of the fully assembled BILI-HUT™ device).

Figure 7:
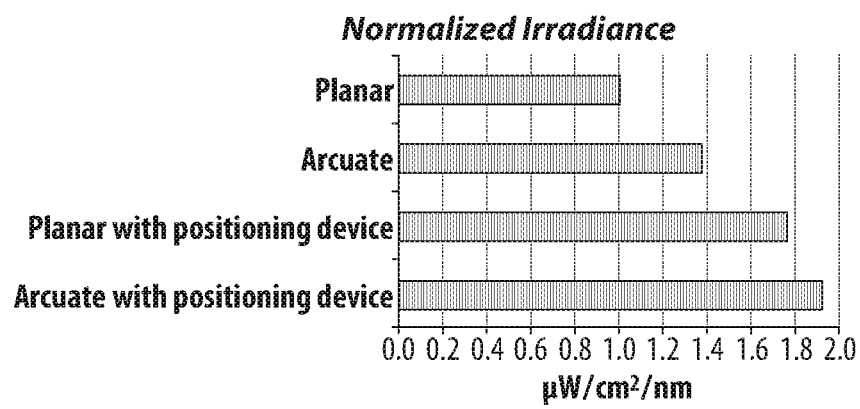
FIG. 7 is a graph showing the relative increase in normalized irradiance to a subject when incorporating a positioning device of the present invention with a phototherapy device.

Results are summarized in FIG. 7. Briefly, when used with a planar configuration of the flexible light array, the subject in the positioning device received an amount of irradiation that was 76% greater than the irradiation received by the subject treated without using the positioning device (1.76 µW/cm2/nm v. 1.0 µW/cm2/nm). When used with the BILI-HUT™ phototherapy device in the assembled arcuate configuration, the subject in the positioning device received an increase in irradiance of 40% (1.92 µW/cm2/nm v. 1.37 µW/cm2/nm) over the irradiance received by a subject treated without using the positioning device. This increase was unexpected when considering that the effect was achieved by positioning the newborn subject model relative to the phototherapy source and not by altering the phototherapy source itself.

Example 3

Positioning Device Incorporating a Visor

This embodiment of the positioning device incorporates all the features of Example 1, with the addition of a visor attached near the head end. The visor is attached in such a manner as to shield the face of a newborn placed inside the positioning device. The function of the visor is to protect the newborn's eyes from being exposed to the blue light during hyperbilirubinemia phototherapy. Use of semi-transparent material to construct the visor allows better visualization of the infant while the infant is receiving phototherapy. For example, the light used to treat hyperbilirubinemia is typically blue light within the wavelength of about 460 nm to 490 nm. The vinyl material used to construct yellow amber welding helmet lens shades may be advantageously used in the construction of a visor for attachment to the positioning device, in that the yellow-orange substrate filters about 99% of light within the blue range (460-490 nm), while filtering only about 50% of other lights, allowing the portions of the subject being shielded to be viewed through the visor. Further, the visor may assist in the thermal regulation of the ambient temperature of the positioning device.

This specific embodiment of the positioning device comprises the elements and features of the positioning device in Example 1, with the addition of the following elements and features:

F. Shade material, which may be opaque or semi-transparent with the property of filtering the desired light wavelength range
   G. Flexible, non-reflective material (Similar to Example 1)
   H. Hook and loop tape
   I. Adhesive backing
   J. Fabric thread (natural or synthetic)

The visor may contain supporting elements, such as plastic or fiberglass rods, or may be constructed of fabric of sufficient rigidity in such a manner as to allow the visor to maintain its shape and position when in use.

Relationship Between the Components

The flexible, non-reflective material (G) is cut in a crescent shape of ~18 inches on one side to extend over the head side of the positioning device. This is considered the head side of the flexible, non-reflective material piece of the visor. From each end of the crescent shape, the flexible, non-reflective material is cut lengthwise approximately seven inches. A crescent shape similar to the original head side crescent shape is cut, joining each of the seven inch lengths, of approximately 18 inches. This is considered the foot side of the visor.

A rectangular window of two-and-a-half inches by four-and-a-half inches is cut in the piece of flexible, non-reflective material from above, such that the four-and-a-half inch side runs parallel to the foot side of the visor, and is centered from approximately one-and-a-half inches from the foot side of the visor. The two-and-a-half inch sides run parallel to the seven inch lengths. A three inch by five inch rectangle of the vinyl lens shade material (F) is cut. A piece of adhesive backing (I) of a width of ½ inch is cut and placed along the perimeter of the cut vinyl lens shade material. The vinyl lens shade material piece is attached to the piece of the flexible, non-reflective material with the adhesive backing on the vinyl lens shade material such that the vinyl lens shade material covers the rectangular window cut into the flexible, non-reflective material. The surface of the material to which the vinyl lens shade is attached is identified as the inner surface of the material.

A length 24 inches is cut from the flexible, fiberglass support rod. The flexible, fiberglass support rod piece is attached to the foot side of the piece of flexible, non-reflective material by wrapping the foot side end of the material over the support rod, and sewing the wrapped material around the rod using thread (J).

Two one-inch square pieces of the flexible, non-reflective material (G) are cut. One of each of these pieces is attached to the outer surface of the positioning device. One is attached to where the head side of the positioning device meets the left side of the positioning device; the other is attached to where the head side of the positioning device meets the right side of the positioning device. The pieces are attached using thread (J). The thread is sewn in such a manner that a pocket of ¾ inch is created on the top side of the individual one inch pieces. These pockets are located on the top-facing sides of the pieces, and are the inserts into which the ends of the fiberglass rod are inserted.

A piece of the hook and loop tape (H) is cut to a length of 18 inches. The loop side of the tape is attached to length of the upper, outer surface of the head side of the positioning device. The hoop side of the tape is attached to the inner surface of the head side of the visor. The flexible, non-reflective material is attached to the positioning device by connecting both sides of the hook and loop tape.

Figure 8:
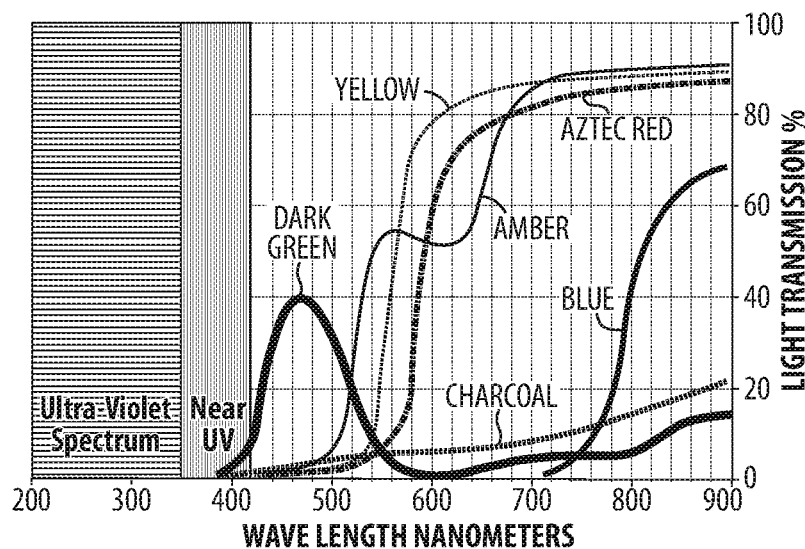
FIG. 8 is a graph showing the percentage of light transmission (versus wavelength) through various visor materials available for use in the phototherapy apparatus described herein. The graph shows that several materials transmit a very low percentage of irradiance at 463 nm (blue) but >50% of irradiance over higher wavelengths of the visible spectrum. Such qualities in a visor would shield the subject's eyes from the incident blue light of the light source yet allow the subject to see through the visor and allow attendants to observe the subject through the visor without difficulty.

The use of the positioning device in this example is similar to the use in Example 1. The newborn's head is placed toward the head side of the positioning device. The window created in the visor allows the newborn subject to be seen by attendants (e.g., the newborn's mother) while receiving phototherapy treatment. Various shade materials are useful but preferably a yellow-amber material is used to create the window shade as it transmits less than one percent of irradiance at blue wavelengths yet has >50% transmission at longer wavelengths, permitting good visibility through the window. The characteristic transmission and attenuation properties of various visor tints is shown in FIG. 8.

Example 4

Thermoregulation Improvements with Positioning Device

Figure 9:
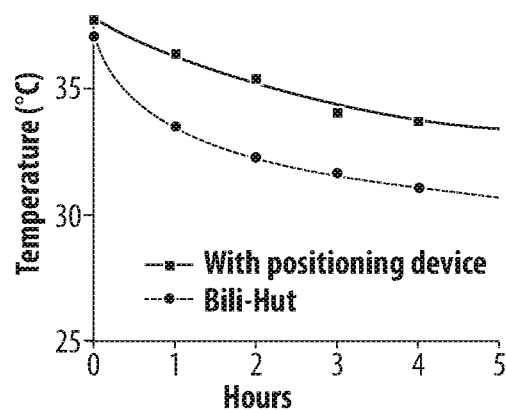
FIG. 9 is a graph showing the relative heat dissipation over time of an embodiment of the positioning device in combination with a phototherapy device versus the relative heat dissipation over time of a phototherapy device without the positioning device.

Testing has shown that utilization of the positioning device in conjunction with the phototherapy device has a positive effect on thermoregulation. A 4.0 L plastic bottle was partially filled with 2.5 L water and a 5 watt heater to simulate surface area, heat capacity, and heat generation of an infant. Over the course of four hours, heat dissipation in a positioning device used within a BILI-HUT™ phototherapy device resulted in a drop in temperature of ~3° C. in a BILI-HUT™, as opposed to a drop in temperature of ~5° C. in a BILI-HUT™ phototherapy device without the positioning device. See FIG. 9.

Example 5

Positioning Device Padding and Vents for Thermoregulation

This embodiment of the positioning device incorporates all the features of Example 3, with the addition of stabilizing padding and side vents.

Vents are present in both the head side and the bottom side, and are located off center. The purpose of the vents is to regulate convectional air flow around the newborn in order to modulate the ambient temperature of the interior of the positioning device.

Padding is connected to the right side and the left side of the positioning device via tethering. The padding serves as a stabilizer for the newborn, allowing the newborn to remain in an optimal position to receive phototherapy treatment from the BILI-HUT™ phototherapy device.

This specific embodiment of the positioning device comprises the elements and features of the positioning device in Example 3, with the addition of following elements and features:

K. Hypoallergenic latex foam

L. Flexible, reflective material (Similar to example 1)

M. Hook and loop tape

N. Fabric thread (natural or synthetic)

O. Louvered vents

P. Adhesive glue

Relationship Between the Components

The hypoallergenic foam (K) is cut into two cylindrical pieces of a length of eight inches and a diameter of two inches each. The flexible, reflective material (L) is cut into two rectangular pieces of approximately nine inches by six-and-a-half inches each. Each piece of hypo-allergenic foam is wrapped with a piece of the material, and the material is sealed around the foam using the fabric thread (N).

Two pieces of hook and loop tape (M) are cut to a length of six inches and a width of ½ inch each. One piece of the loop portion of the tape is centered and attached lengthwise to the inner surface of the left side of the positioning device. The corresponding hook portion of the tape is attached along the centered length of one of the pieces of covered foam. These steps are repeated on the inner surface of the right side of the positioning device and the other piece of covered foam. The pieces of covered foam are attached to the inner surface of the positioning device using the installed hook and loop tape.

Four circular, plastic three inch diameter louvered vents (N) of a type similar to the vents available from Five Oceans Machine Products (http://www.five-oceans.com/; catalogue code 110) are used to create vents located on both the head end and the foot end of the positioning device.

Two three-inch diameter circular holes are cut into the head end of the positioning device: one four inches left of the center of the head end, the other four inches right of the center of the head side. Similarly, two three-inch diameter circular holes are cut into the foot side of the positioning device: one four inches left of the center of the foot side, the other four inches right of the center of the foot side. The four louvered vents are attached to the outer surface of the positioning device in the holes created using the adhesive glue (P).

The purpose of the foam inserts in the positioning device is to stabilize the infant in an optimal location in which to receive phototherapy. The reflective material used to cover the foam will increase the amount of electromagnetic radiation received by the newborn.

The vents in the positioning device are directed at optimizing passive convective air flow through the course of the infant's occupation of the positioning device.

Example 6

Positioning Device Thermal Unit for Thermoregulation

This embodiment of the positioning device incorporates all the features of Example 3, with the addition of a thermal unit.

When used in colder locations, it may be necessary to add a thermal unit to the positioning device in order for the subject to maintain adequate body temperature. The thermal unit serves to modulate the ambient temperature of the positioning device. The thermal unit is placed within a pocket created in the bottom side of the positioning device.

Warming thermal devices are readily available commercially. In the current example, the thermal unit used is a nine inch by 12 inch by ½ inch thermal heated pad designed to keep pets warm. The thermal heating pad is powered by alternating current. The product is sold by Drs. Foster and Smith (Rhinelander, Wis.).

This specific embodiment of the positioning device comprises the elements and features of the positioning device in Example 3, with the addition of following elements and features:

Q. Hook and loop tape

R. Powered heat pad

S. Power supply

Relationship Between the Components

Using the positioning device in Example 3, a 15 inch slit is made lengthwise in the center of the right portion of the bottom side of the positioning device located below where the bottom side of the positioning device is attached to the right side of the positioning device. A 14 inch length of ½ inch wide hook and loop tape (Q) is cut. The hook side of the hook and loop tape is attached lengthwise to the bottom of the slit created in the bottom side of the positioning device. The loop side of the hook and loop tape is attached lengthwise to the top of the slit created in the bottom side of the positioning device in such a manner that it may come in contact with the hook side of the hook and loop tape.

The heat pad (R) is inserted into the bottom side of the positioning device in between the layer of insulation and the bottom of the inner surface of the bottom side. The power cord of the heat pad is plugged into the power supply (S). The hook and loop tape is sealed.

The material used for the inner surface (as described in Example 1, above) is chosen to be 40 gauge vinyl, in order to minimize any discomfort to the newborn as a result of the insertion of the heating pad. The heating pad selected will heat to a maximum of 39° C., which will allow the positioning device to maintain a temperate environment without the possibility of inflicting burns upon the newborn.

The use of this example is similar to the use of Example 3.

The exemplary embodiments described herein are not intended to be exhaustive or to limit the scope of the invention to the precise forms disclosed. Those skilled in the art understand the inventive principles and concepts of the present invention disclosed and enabled by this specification, and appreciate that equivalents, alterations, and modifications of the elements and features of the present invention exist in the practice of this invention without departing from the spirit or scope thereof. For example, the various elements necessary to construct the positioning device of the present invention are defined by their necessary functional properties, and not limited, unless otherwise specified herein, by any particular composition of matter or structure. The terms used to describe such elements are intended to correspond, to any element capable of performing the defined necessary function of the described element. The metes and bounds of the invention are to be construed in accordance with the following claims. The publications cited herein are hereby incorporated by reference.

We claim:

1. A compound portable phototherapy device adapted for the treatment of hyperbilirubinemia, comprising separable parts I and II, part I of said compound portable phototherapy device comprising:
(a) a floor section essentially rectangular in shape defined by a head end and a foot end and two sides, said floor being dimensioned so as to support the length of a reclining infant of up to about five kilograms, said floor having a fold-over tab attached along at least a portion of one side of the floor, the tab exhibiting one or more fasteners along its length;
(b) a canopy section attached to said floor section along the side of the floor section opposite said fold-over tab, said canopy section extending from a proximal end attached to said floor section to a distal edge, said canopy section exhibiting one or more fasteners near its distal edge capable of mating with the corresponding fasteners on said fold-over tab to securely but reversibly join said distal edge of the canopy section to said fold-over tab, said canopy section being dimensioned such that joining said distal edge of the canopy section with the fold-over tab attached to said floor section forms an arcuate shell over said floor section, defining an assembled configuration having an inner surface facing said floor section and an outer surface;
(c) a plurality of light sources affixed to the inner surface of said shell, said plurality of light sources being capable of emitting light of a wavelength of 400-550 nm;
(d) an electrical power source;
(e) circuitry operably connecting said power source to said plurality of light sources; and
(f) one or more frame support elements affixed to said canopy section which are flexible yet rigid enough to support said canopy section in an arcuate shell configuration;
wherein the inner surface of said shell comprises a reflective surface; and wherein said floor section, fold-over tab, and canopy sections are of a pliable material such that, when said fasteners are not fastened, said floor section, tab, and canopy section, together with said affixed plurality of light sources and frame support elements are capable of being flattened or rolled or compressed to a disassembled size smaller than that of its operating size;

part II of said compound portable phototherapy device comprising:
(a) a collapsible positioning device dimensioned to encompass an infant of up to about five kilograms and dimensioned to fit within the enclosure of part I of said compound portable phototherapy device, said positioning device having an interior concave shape defined by a floor and raised sides defining left and right sides, a foot end, and a head end, at least a portion of the inner surface of said positioning device comprising a reflective surface, wherein said head end has a height greater than the height of the shortest side of the device and wherein said foot end has a height greater than the height of the shortest side of the device, and wherein said collapsible positioning devices can be flattened, folded rolled or compressed to a size that is less than the working space of the positioning device in its operational configuration; and
(b) optionally, affixed over the head end of said positioning device, a visor positioned so as to mask the eyes of an infant placed in said positioning device from light emitted from outside of the positioning device;
wherein said positioning device is capable of reflecting light onto said subject from a light source located outside of said positioning device; and
wherein, in the assembled configuration, said plurality of light sources is capable of transmitting light of sufficient intensity and wavelength to provide a desired phototherapeutic effect to an infant positioned in said positioning device which in turn is positioned on the floor section, without said plurality of light sources of part I of said compound portable phototherapy device being in direct physical contact with said infant.

2. The compound portable phototherapy device of claim 1, wherein said part I is capable of being compressed to a disassembled configuration of a size smaller than that of its operating configuration.

3. The compound portable phototherapy device of claim 1, wherein said positioning device further comprises a visor.

4. The compound portable phototherapy device of claim 3, wherein said visor is attached to the head side of the positioning device.

5. The compound portable phototherapy device of claim 3, wherein said visor is retractable.

6. The compound portable phototherapy device of claim 3, wherein said visor is positioned to form a partial top side of said positioning device.

7. The compound portable phototherapy device of claim 3, wherein said visor is semitransparent.

8. The compound portable phototherapy device of claim 3, wherein said visor functions to filter said light onto a portion of said subject.

9. The compound portable phototherapy device of claim 8, wherein said visor filters out blue and ultraviolet light.

10. The compound portable phototherapy device of claim 1, wherein at least one of said sides of said positioning device comprises a vent.

11. The compound portable phototherapy device of claim 1, wherein at least one of said sides of said positioning device comprises a stabilizing insert.

12. The compound portable phototherapy device of claim 1, wherein said inner surface of said positioning device is a non-porous surface.

13. The compound portable phototherapy device of claim 12, wherein said non-porous surface is medical grade vinyl.

14. The compound portable phototherapy device of claim 1, wherein said positioning device comprises a removable liner.

15. The compound portable phototherapy device of claim 1, wherein said positioning device further comprises a thermal element.

16. The compound portable phototherapy device of claim 15, wherein said thermal element is capable of modulating the temperature inside of said phototherapy device.

17. The compound portable phototherapy device of claim 16, wherein said thermal element is a heating element.

18. The compound portable phototherapy device of claim 15, wherein said thermal element comprises a thermostable gel.

19. The compound portable phototherapy device of claim 1, wherein the compressible positioning device is adapted to be detachable from part 1 of said compound portable phototherapy device.

* * * * *